United States Patent
Moody, III et al.

(10) Patent No.: US 12,233,633 B2
(45) Date of Patent: Feb. 25, 2025

(54) ACQUISITION DISTRIBUTION LAYER

(71) Applicant: Berry Global, Inc., Evansville, IN (US)

(72) Inventors: Ralph A. Moody, III, Mooresville, NC (US); Andrew W. Delaney, Allentown, NJ (US); Luca Ferrandi, Bergamo (IT); Robert Garcia, Alcanar (ES)

(73) Assignee: BERRY GLOBAL, INC., Evansville, IN (US)

( * ) Notice: Subject to any disclaimer, the term of this patent is extended or adjusted under 35 U.S.C. 154(b) by 0 days.

(21) Appl. No.: 17/377,828

(22) Filed: Jul. 16, 2021

(65) Prior Publication Data
US 2022/0016867 A1 Jan. 20, 2022

Related U.S. Application Data

(60) Provisional application No. 63/052,966, filed on Jul. 17, 2020.

(51) Int. Cl.
*B32B 5/22* (2006.01)
*B32B 5/02* (2006.01)
*B32B 5/06* (2006.01)
*B32B 5/26* (2006.01)

(52) U.S. Cl.
CPC .............. *B32B 5/067* (2021.05); *B32B 5/022* (2013.01); *B32B 5/267* (2021.05);
(Continued)

(58) Field of Classification Search
CPC ......... B32B 5/067; B32B 5/267; B32B 5/022; B32B 2555/02; B32B 2307/718;
(Continued)

(56) References Cited

U.S. PATENT DOCUMENTS

| | | | | |
|---|---|---|---|---|
| 5,895,623 A | * | 4/1999 | Trokhan | D04H 1/64 28/106 |
| 6,314,627 B1 | * | 11/2001 | Ngai | B32B 5/26 28/104 |

(Continued)

FOREIGN PATENT DOCUMENTS

| | | |
|---|---|---|
| WO | 2002004729 A1 | 1/2002 |
| WO | 2014186570 A1 | 11/2014 |
| WO | 2020004995 A1 | 1/2020 |

OTHER PUBLICATIONS

International Search Report and Written Opinion of corresponding international application No. PCT/US2021/041964 mailed on Oct. 22, 2021, all enclosed pages cited.

(Continued)

*Primary Examiner* — Matthew D Matzek
(74) *Attorney, Agent, or Firm* — BURR & FORMAN LLP

(57) ABSTRACT

Acquisition-distribution-layers (ADL) comprising a hydroentangled composite are provided. The hydroentangled composite includes (a) a first outer layer including a first plurality of synthetic fibers, (b) a second outer layer including a second plurality of synthetic fibers, and (c) at least one core layer including cellulose fibers comprising natural cellulose fibers, synthetic cellulose fibers, or a combination thereof, in which the at least one core layer is located directly or indirectly between the first outer layer and the second outer layer. The first plurality of synthetic fibers, the second plurality of synthetic fibers, and the cellulose fibers are physically entangled together. The hydroentangled composite further comprises a three-dimensional topography defined by a first outermost surface of the hydroentangled composite, in which the three-dimensional topography includes a plurality raised portions and a plurality of recessed portions.

21 Claims, 10 Drawing Sheets

(52) U.S. Cl.
CPC ... *B32B 2307/718* (2013.01); *B32B 2307/726* (2013.01); *B32B 2307/732* (2013.01); *B32B 2555/02* (2013.01)

(58) Field of Classification Search
CPC ........ B32B 2307/726; B32B 2307/732; B32B 2262/02; B32B 2262/0253; B32B 5/266; B32B 2250/03; B32B 2250/20; B32B 2262/04; A61F 13/53717; A61F 13/53747; D04H 1/495; D04H 1/498
USPC .................................................. 442/384, 408
See application file for complete search history.

(56) References Cited

U.S. PATENT DOCUMENTS

| | | | |
|---|---|---|---|
| 6,735,833 B2 | 5/2004 | Putnam et al. | |
| 6,903,034 B1 | 6/2005 | Putnam et al. | |
| 7,091,140 B1 | 8/2006 | Ferencz et al. | |
| 7,406,755 B2 | 8/2008 | Putnam et al. | |
| 2009/0157036 A1* | 6/2009 | Ponomarenko | B32B 38/0012 604/385.24 |
| 2014/0121621 A1* | 5/2014 | Kirby | A61F 13/5126 604/374 |
| 2018/0369028 A1* | 12/2018 | Cecchetto | A61F 13/5123 |

OTHER PUBLICATIONS

Third Written Opinion of corresponding international application No. PCT/US2021/041964 mailed on Sep. 2, 2022, all enclosed pages cited.

Second Written Opinion of corresponding international application No. PCT/US2021/041964 mailed on May 30, 2022, all enclosed pages cited.

* cited by examiner

ACQUISITION DISTRIBUTION LAYER

CROSS-REFERENCE TO RELATED APPLICATIONS

This application claims priority under 35 U.S.C. § 119(e) to U.S. Provisional Application No. 63/052,966 filed Jul. 17, 2020, which is expressly incorporated by reference herein in its entirety.

TECHNICAL FIELD

Embodiments of the presently-disclosed invention relate generally to acquisition distribution layers (ADL) comprising a hydroentangled composite including outer layers of synthetic fibers physically entangled with cellulose fibers of at least one core layer, in which the hydroentangled composite includes a three-dimensional topography defined by a first outermost surface of the hydroentangled composite. Embodiments of the presently-disclosed invention also relate to methods of forming such ADLs and hygiene articles including such ADLs.

BACKGROUND

An absorbent article typically comprises a topsheet, a backsheet, and an absorbent core disposed between the topsheet and the backsheet. The absorbent article can further include an acquisition web alone or in combination with a distribution layer. The acquisition web generally receives liquid bodily exudates from the topsheet in order to temporary store them. Then, the distribution layer can receive the liquid bodily exudates from the acquisition web and distribute and transfer them to the absorbent core. In this regard, the combination of the acquisition web and the distribution layer should ideally guarantee prompt passage of liquids into the absorbent core and fast liquid distribution and absorption into a wide area of the absorbent core.

There remains a need in the art for an ADL, for example, for hygiene-related applications that are capable of promptly absorbing a fluid and/or distributing the fluid across a desirable area of an absorbent core located underneath the ADL.

SUMMARY OF INVENTION

One or more embodiments of the invention may address one or more of the aforementioned problems. Certain embodiments according to the invention provide an acquisition-distribution-layer (ADL) comprising a hydroentangled composite comprising (a) a first outer layer including a first plurality of synthetic fibers, (b) a second outer layer including a second plurality of synthetic fibers, and (c) at least one core layer including cellulose fibers comprising natural cellulose fibers, synthetic cellulose fibers, or a combination thereof, wherein the at least one core layer is located directly or indirectly between the first outer layer and the second outer layer. In accordance with certain embodiments of the invention, the first plurality of synthetic fibers, the second plurality of synthetic fibers, and the cellulose fibers are physically entangled together. The hydroentangled composite, in accordance with certain embodiments of the invention, may further comprise a three-dimensional topography defined by a first outermost surface of the hydroentangled composite, wherein the three-dimensional topography includes a plurality raised portions and a plurality of recessed portions.

In another aspect, the present invention provides a method of making an ADL including steps of (a) providing a first outer layer including a first plurality of synthetic fibers; (b) providing a second outer layer including a second plurality of synthetic fibers; (c) providing at least one core layer including cellulose fibers comprising natural cellulose fibers, synthetic cellulose fibers, or a combination thereof, wherein the at least one core layer is located directly or indirectly between the first outer layer and the second outer layer; (d) physically entangling the first plurality of synthetic fibers, the second plurality of synthetic fibers, and the cellulose fibers together to form a hydroentangled composite; and (e) imparting a three-dimensional topography defined by a first outermost surface of the hydroentangled composite; wherein the three-dimensional topography includes a plurality raised portions and a plurality of recessed portions.

In another aspect the present invention provides a hygiene article. In accordance with certain embodiments of the invention, the hygiene article comprises a longitudinal axis and a transversal axis perpendicular to the longitudinal axis. The hygiene article further comprises an ADL, such as those described and disclosed herein, a liquid impermeable backsheet, and an absorbent core, in which the absorbent core is located at least partially between the ADL and the backsheet.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein:

FIG. 1A illustrates a cross-sectional view of a hydroentangled composite in accordance with certain embodiments of the invention;

FIG. 1B also illustrates a cross-sectional view of a hydroentangled composite in accordance with certain embodiments of the invention;

Figure 5:
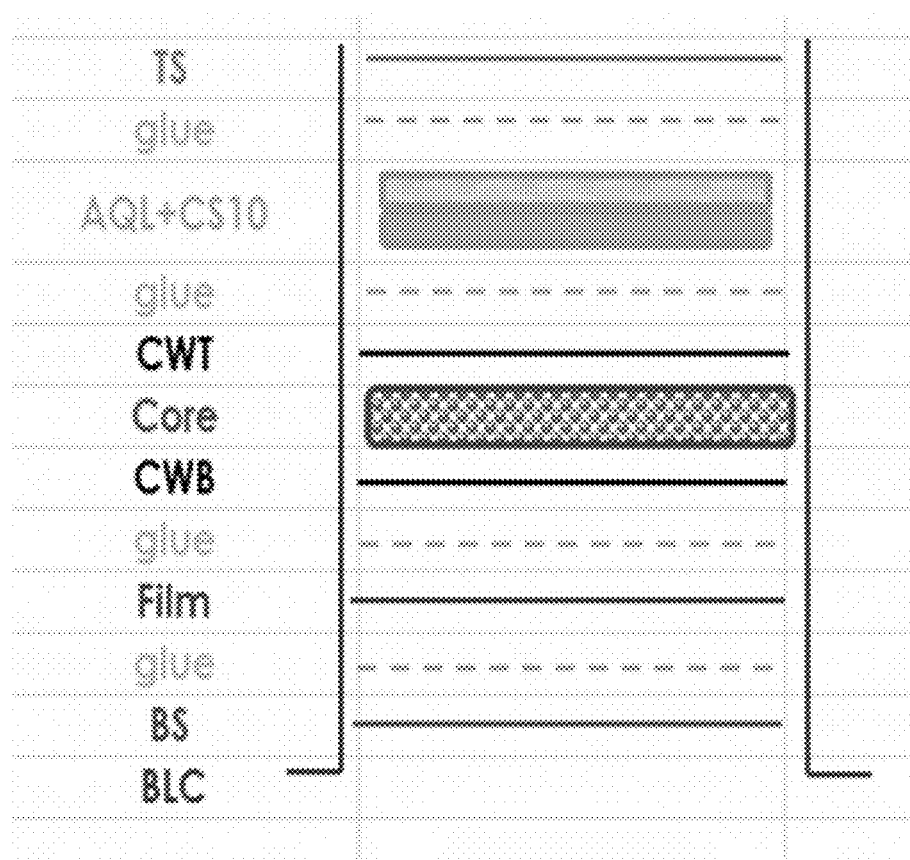
Figure 6:
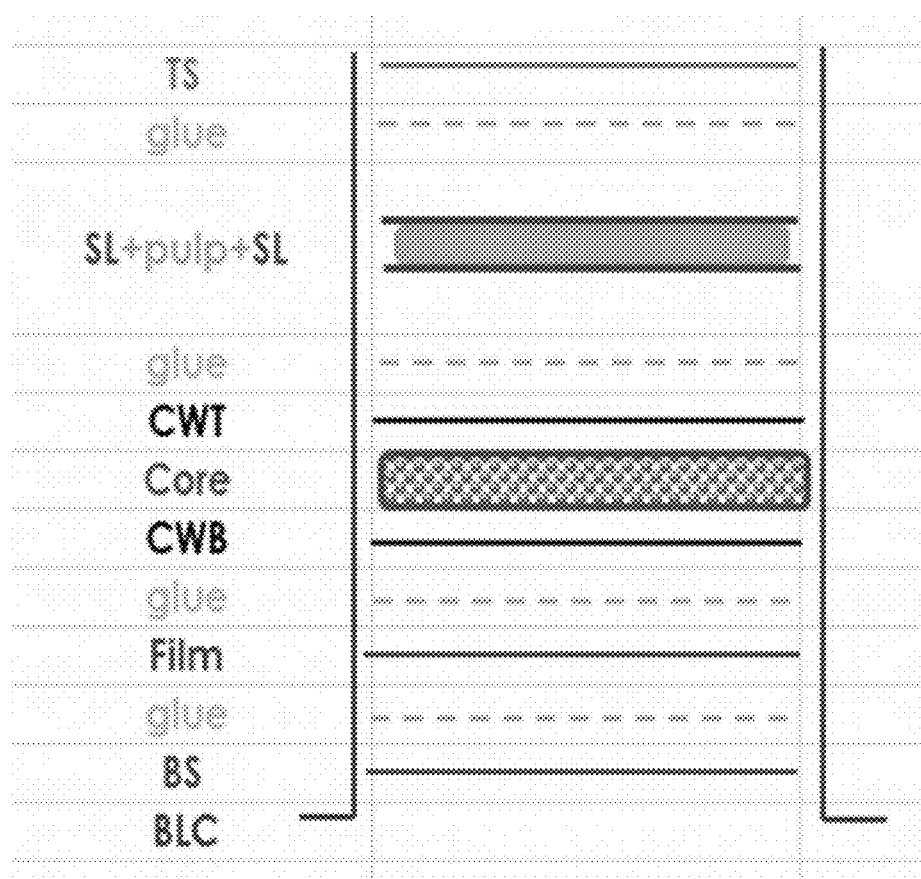
Figure 7:
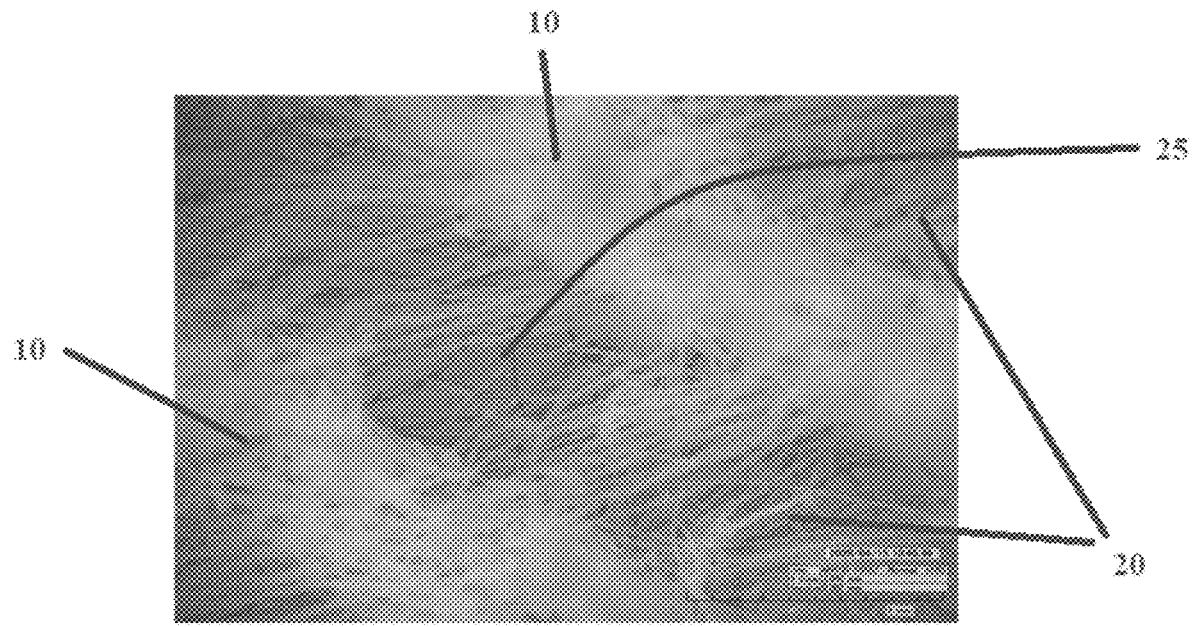
Figure 8:
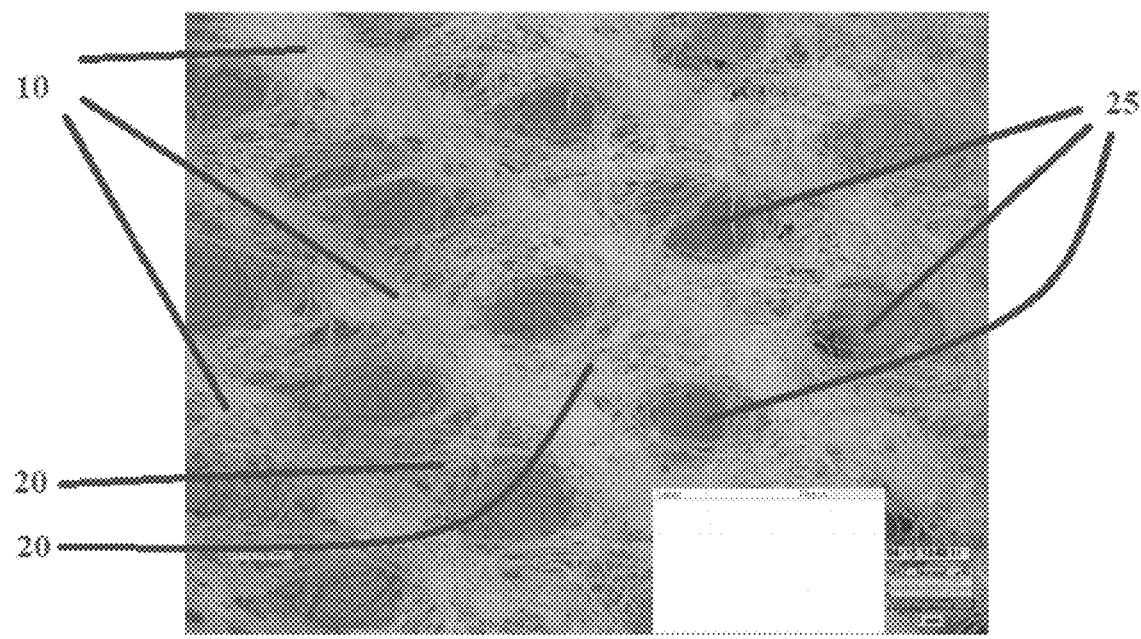

FIG. 5 provides a schematic of a standard or reference diaper construction;

FIG. 6 provides a schematic of a diaper construction in accordance with certain embodiments of the invention;

FIG. 7 shows an 80 gsm hydroentangled composite in accordance with certain embodiments of the invention; and FIG. 8 shows an 80 gsm hydroentangled composite in accordance with certain embodiments of the invention.

DETAILED DESCRIPTION

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The presently-disclosed invention relates generally to ADLs comprising a hydroentangled composite, in which the hydroentangled composite comprises a blend of physically entangled synthetic fibers and cellulose fibers (e.g., natural and/or synthetic). In accordance with certain embodiments of the invention, the ADL provides a desirably high capture rate for a fluid (e.g., urine, blood, etc.) and/or a desirably low rewet value. In accordance with certain embodiments of the invention, the hydroentangled composite may include a three-dimensional image (e.g., topography extending outwardly from the hydroentangled composite into the z-direction) imparted into one or both sides of the hydroentangled composite. In accordance with certain embodiments of the invention, the three-dimensional image includes a plurality of raised portions and a plurality of recessed portions defining a pattern that may facilitate the rapid capture of a fluid as well as efficient distribution of the fluid to a large area of an absorbent core located directly or indirectly below the hydroentangled composite. For instance, a fluid (e.g., urine) may strike the ADL directly or through passage of a topsheet at a first area. The ADL may simultaneously channel the fluid across an area larger than the first area while capturing and/or passing (e.g., acquisition rate) the fluid through the ADL to an absorbent core layer(s). In accordance with certain embodiments of the invention, the porosity of the hydroentangled composite may be increased by incorporating a plurality of apertures that facilitate rapid acquisition of the fluid.

The terms "substantial" or "substantially" may encompass the whole amount as specified, according to certain embodiments of the invention, or largely but not the whole amount specified (e.g., 95%, 96%, 97%, 98%, or 99% of the whole amount specified) according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include, in according to certain embodiments of the invention, polymers produced by fermentation process or biosourced.

The term "cellulose fiber", as used herein, may comprise fibers including or formed from natural cellulose, regenerated cellulose (e.g., synthetic), and/or combinations thereof. For example, a "cellulose fiber" may be derived from hardwood trees, softwood trees, or a combination of hardwood and softwood trees prepared for use in, for example, a papermaking furnish and/or fluff pulp furnish by any known suitable digestion, refining, and bleaching operations. The cellulose fibers may comprise recycled fibers and/or virgin fibers. Recycled fibers differ from virgin fibers in that the fibers have gone through the drying process at least once. In certain embodiments, at least a portion of the cellulose fibers may be provided from non-woody herbaceous plants including, but not limited to, kenaf, cotton, hemp, jute, flax, sisal, or abaca. Cellulose fibers may, in certain embodiments of the invention, comprise either bleached or unbleached pulp fiber such as high yield pulps and/or mechanical pulps such as thermo-mechanical pulping (TMP), chemical-mechanical pulp (CMP), and bleached chemical-thermo-mechanical pulp BCTMP. In this regard, the term "pulp", as used herein, may comprise cellulose that has been subjected to processing treatments, such as thermal, chemical, and/or mechanical treatments. Cellulose fibers, according to certain embodiments of the invention, may comprise one or more pulp materials. In accordance with certain embodiments of the invention, the cellulose fibers may comprise a rayon, such as viscose.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, needle-punching, hydroentangling, air-laid, and bonded carded web processes. A "nonwoven web", as used herein, may comprise a plurality of individual fibers that have not been subjected to a consolidating process.

The terms "fabric" and "nonwoven fabric", as used herein, may comprise a web of fibers in which a plurality of the fibers are mechanically entangled or interconnected, fused together, and/or chemically bonded together. For example, a nonwoven web of individually laid fibers may be subjected to a bonding or consolidation process to bond at least a portion of the individually fibers together to form a coherent (e.g., united) web of interconnected fibers.

The term "consolidated" and "consolidation", as used herein, may comprise the bringing together of at least a portion of the fibers of a nonwoven web into closer proximity or attachment there-between (e.g., thermally fused together, chemically bonded together, and/or mechanically entangled together) to form a bonding site, or bonding sites, which function to increase the resistance to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., thermally fused together, chemically bonded together, and/or mechanically entangled together), such as by thermal bonding or mechanical entanglement (e.g., hydroentanglement) as merely a few examples. Such a web may be considered a "consolidated nonwoven", "nonwoven fabric" or simply as a "fabric" according to certain embodiments of the invention.

The term "staple fiber", as used herein, may comprise a cut fiber from a filament. In accordance with certain embodiments, any type of filament material may be used to form staple fibers. For example, staple fibers may be formed from polymeric fibers, and/or elastomeric fibers. Non-limiting examples of materials may comprise polyolefins (e.g., a polypropylene or polypropylene-containing copolymer), polyethylene terephthalate, and polyamides. The average length of staple fibers may comprise, by way of example only, from about 2 centimeter to about 15 centimeter.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous as disclosed and described herein. It is noted that the spunbond used in certain composites of the invention may include a nonwoven described in the literature as SPINLACE®. Spunbond fibers, for example, may comprises continuous fibers.

As used herein, the term "continuous fibers" refers to fibers which are not cut from their original length prior to being formed into a nonwoven web or nonwoven fabric. Continuous fibers may have average lengths ranging from greater than about 15 centimeters to more than one meter, and up to the length of the web or fabric being formed. For example, a continuous fiber, as used herein, may comprise a fiber in which the length of the fiber is at least 1,000 times larger than the average diameter of the fiber, such as the length of the fiber being at least about 5,000, 10,000, 50,000, or 100,000 times larger than the average diameter of the fiber.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers may comprise microfibers which may be continuous or discontinuous and are generally tacky when deposited onto a collecting surface. Meltblown fibers, however, are shorter in length than those of spunbond fibers.

The term "layer", as used herein, may comprise a generally recognizable combination of similar material types and/or functions existing in the X-Y plane.

The term "multi-component fibers", as used herein, may comprise fibers formed from at least two different polymeric materials or compositions (e.g., two or more) extruded from separate extruders but spun together to form one fiber. The term "bi-component fibers", as used herein, may comprise fibers formed from two different polymeric materials or compositions extruded from separate extruders but spun together to form one fiber. The polymeric materials or polymers are arranged in a substantially constant position in distinct zones across the cross-section of the multi-component fibers and extend continuously along the length of the multi-component fibers. The configuration of such a multi-component fiber may be, for example, a sheath/core arrangement wherein one polymer is surrounded by another, an eccentric sheath/core arrangement, a side-by-side arrangement, a pie arrangement, or an "islands-in-the-sea" arrangement, each as is known in the art of multicomponent, including bicomponent, fibers.

The term "machine direction" or "MD", as used herein, comprises the direction in which the fabric produced or conveyed. The term "cross-direction" or "CD", as used herein, comprises the direction of the fabric substantially perpendicular to the MD.

The term "crimp" or "crimped", as used herein, comprises a three-dimensional curl or bend such as, for example, a folded or compressed portion having an "L" configuration, a wave portion having a "zig-zag" configuration, or a curl portion such as a helical configuration. In accordance with certain embodiments of the invention, the term "crimp" or "crimped" does not include random two-dimensional waves or undulations in a fiber, such as those associated with normal lay-down of fibers in a melt-spinning process.

As used herein, the term "continuous fibers" refers to fibers which are not cut from their original length prior to being formed into a nonwoven web or nonwoven fabric. Continuous fibers may have average lengths ranging from greater than about 15 centimeters to more than one meter, and up to the length of the web or fabric being formed. For example, a continuous fiber, as used herein, may comprise a fiber in which the length of the fiber is at least 1,000 times larger than the average diameter of the fiber, such as the length of the fiber being at least about 5,000, 10,000, 50,000, or 100,000 times larger than the average diameter of the fiber.

As used herein, the term "aspect ratio", comprise a ratio of the length of the major axis to the length of the minor axis of the cross-section of the fiber in question.

All whole number end points disclosed herein that can create a smaller range within a given range disclosed herein are within the scope of certain embodiments of the invention. By way of example, a disclosure of from about 10 to about 15 includes the disclosure of intermediate ranges, for example, of: from about 10 to about 11; from about 10 to about 12; from about 13 to about 15; from about 14 to about 15; etc. Moreover, all single decimal (e.g., numbers reported to the nearest tenth) end points that can create a smaller range within a given range disclosed herein are within the scope of certain embodiments of the invention. By way of example, a disclosure of from about 1.5 to about 2.0 includes the disclosure of intermediate ranges, for example, of: from about 1.5 to about 1.6; from about 1.5 to about 1.7; from about 1.7 to about 1.8; etc.

Certain embodiments according to the invention provide an ADL comprising a hydroentangled composite comprising (a) a first outer layer including a first plurality of synthetic fibers, (b) a second outer layer including a second plurality of synthetic fibers, and (c) at least one core layer including cellulose fibers comprising natural cellulose fibers, synthetic cellulose fibers, or a combination thereof, wherein the at least one core layer is located directly or indirectly between the first outer layer and the second outer layer. In accordance with certain embodiments of the invention, the first plurality of synthetic fibers, the second plurality of synthetic fibers, and the cellulose fibers are physically entangled together.

The hydroentangled composite, in accordance with certain embodiments of the invention, may further comprise a three-dimensional topography defined by a first outermost surface of the hydroentangled composite; wherein the three-dimensional topography includes a plurality raised portions and a plurality of recessed portions.

Figure 1A:
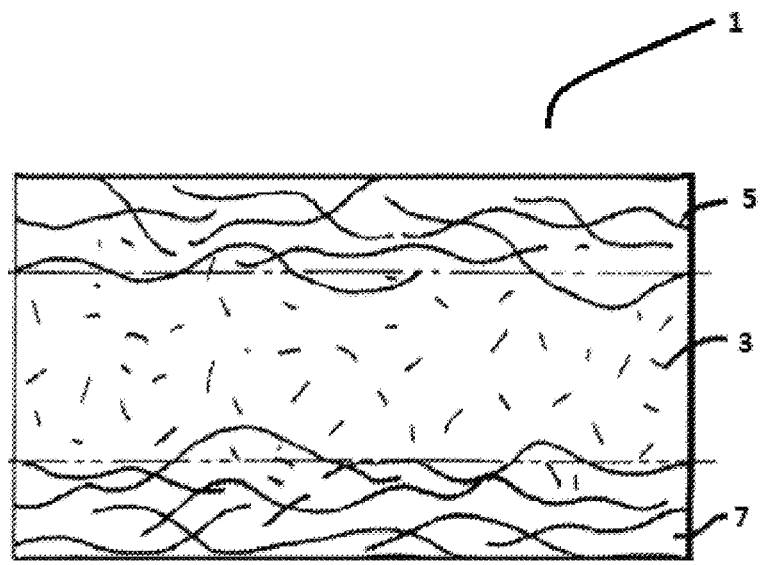
Figure 1B:
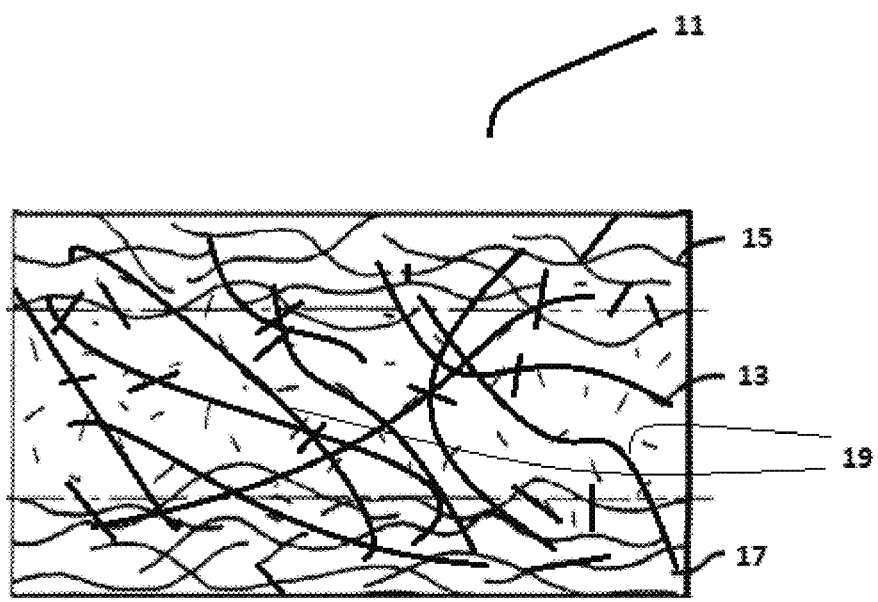

FIG. 1A, for example, illustrates a cross-sectional view of a hydroentangled composite 1 in accordance with certain embodiments of the invention, in which the hydroentangled composite 1 includes a layer of cellulose fibers 3 (e.g., pulp) positioned between a first outer layer 5 (e.g., nonwoven web or nonwoven fabric) and a second outer layer 7 (e.g., nonwoven web or nonwoven fabric). As illustrated by FIG. 1A, fibers of the first outer layer 5 may be physically entangled with the layer of cellulose fibers 3, and the second outer layer 7 may also be physically entangled with the layer of cellulose fibers 3. FIG. 1A, for instance, may illustrate a hydroentangled composite subjected to relatively light physical entanglement operation (e.g., hydroentanglement). FIG. 1B, for example, illustrates a cross-sectional view of a hydroentangled composite 11 in accordance with certain embodiments of the invention, in which the hydroentangled composite fabric 11 also includes a layer of cellulose fibers 13 (e.g., pulp) positioned between a first outer layer 15 and a second outer layer 17. As illustrated by FIG. 1B, fibers of the first outer layer 15 may be physically entangled with the layer of cellulose fibers 13, and the second outer layer 17 may also be physically entangled with the layer of cellulose fibers 13. FIG. 1B also illustrates a plurality of synthetic fibers 19 spanning nearly the entire thickness of the hydroentangled composite 11. In this regard, fibers from the first outer layer 15, fibers from the second outer layer 17, and the cellulose fibers 13 are all hydroentangled together to provide a more homogenous distribution of fibers across the thickness of the hydroentangled composite. In accordance with certain embodiments of the invention and as shown in FIG. 1B, the concentration of the cellulose fibers 3 may still be greatest at or near the middle of the thickness in the z-direction of the hydroentangled composite. In accordance with certain embodiments of the invention, the first and second outer layers may comprise thermal bond sites, such as by thermal calendering, in addition to being physically entangled alone or with fibers from an additional layer of natural and/or synthetic fibers.

In accordance with certain embodiments of the invention, the first outer layer, the second outer layer, or both independently from each other comprise a spunbond layer, a meltblown layer, or a carded layer. For example, the first outer layer may comprise a carded layer while the second outer layer may comprise a spunbond layer. In accordance with certain embodiments of the invention, the synthetic fibers of the first outer layer, second layer, or both may comprise crimped fibers, non-crimped fibers, or any combination thereof.

In accordance with certain embodiments of the invention, the first plurality of synthetic fibers of the first outer layer may comprise a synthetic polymeric material, such as a polyolefin, a polyester, a polyamide, or any combination thereof. For example, the first plurality of synthetic fibers may comprise a polypropylene, a polypropylene copolymer, a polyethylene, a polyethylene copolymer, or any combination thereof. In accordance with certain embodiments of the invention, the first plurality of synthetic fibers may be blended with fibers formed from a biopolymer, such as polylactic acid (PLA), polyhydroxyalkanoates (PHA), and poly(hydroxycarboxylic) acids. In this regard, the first outer layer may comprise both fibers formed from a synthetic polymeric material and fibers formed from a biopolymer.

In accordance with certain embodiments of the invention, the second plurality of synthetic fibers of the second outer layer may comprise a synthetic polymeric material, such as a polyolefin, a polyester, a polyamide, or any combination thereof. For example, the second plurality of synthetic fibers may comprise a polypropylene, a polypropylene copolymer, a polyethylene, a polyethylene copolymer, or any combination thereof. In accordance with certain embodiments of the invention, the second plurality of synthetic fibers may be blended with fibers formed from a biopolymer, such as polylactic acid (PLA), polyhydroxyalkanoates (PHA), and poly(hydroxycarboxylic) acids. In this regard, the second outer layer may comprise both fibers formed from a synthetic polymeric material and fibers formed from a biopolymer.

In accordance with certain embodiments of the invention, the first plurality of synthetic fibers, the second plurality of synthetic fibers, or both may comprise monocomponent fibers, multi-component fibers (e.g., bicomponent fibers), or both. Additionally or alternatively, the first plurality of synthetic fibers, the second plurality of synthetic fibers, or both may comprise a round cross-section, a non-round cross-section, or a combination thereof. In this regard, fibers having a round cross-section may have an aspect ratio of from about 0.8 to about 1.2, while non-round cross-sectional fibers may have an aspect ratio exceeding 1.2, such as exceeding about 1.5. Additionally or alternatively, fibers formed either entirely or at least in part from a biopolymer may also be provided as monocomponent fibers and/or multicomponent fibers, which may also have the same aspect ratios noted above.

In accordance with certain embodiments of the invention, the hydroentangled composite may comprise a basis weight from about 20 to about 100 grams-per-square (gsm), such as from at least about any of the following: 20, 30, 40, 50, and 60 gsm and/or at most about any of the following: 100, 90, 80, 70, 60, and 50 gsm. In accordance with certain embodiments of the invention, the at least one core layer comprises from about 40% by wt. to about 80% by wt. of the hydroentangled composite, such as from at least about any of the following: 40, 45, 50, 55, and 60% by wt. of the hydroentangled composite and/or at most about any of the following: 80, 75, 70, 65, and 60% by wt. of the hydroentangled composite.

The at least one core layer, for example, may be devoid of synthetic fibers. Alternatively, the at least one core layer may comprise synthetic core-fibers. For example, the synthetic core-fibers may comprise one or more synthetic polymeric materials, such as a polypropylene, a polypropylene copolymer, a polyethylene, a polyethylene copolymer, or any combination thereof. Additionally or alternatively, the at least one core layers may include biopolymer core-fibers formed from a biopolymer, such as polylactic acid (PLA), polyhydroxyalkanoates (PHA), and poly(hydroxycarboxylic) acids. In accordance with certain embodiments of the invention, the synthetic core-fibers and/or the biopolymer core-fibers (if either is present) may comprise continuous spunbond fibers, discontinuous meltblown fibers, staple fibers, or any combination thereof.

In accordance with certain embodiments of the invention, the at least one core layer may comprise from about 20 wt. % to about 100% by wt. of the cellulose fibers, such as at least about any of the following: 20, 30, 40, 50, 60, 70, 80, and 90% by wt. and/or at most about any of the following: 100, 99, 98, 95, 90, 85, 80, 75, and 70% by wt.

The hydroentangled composite, in accordance with certain embodiments of the invention, has a total thickness in a z-direction, which is orthogonal to a machine-direction and a cross-direction of the hydroentangled composite. The at least one core layer, in accordance with certain embodiments of the invention, may comprise from about 10% to about 60% of the total thickness, such as from at least about any of the following: 10, 15, 20, 25, 30, 35, and 40% of the total thickness and/or from at most about any of the following: 60, 55, 50, 45, 40, 35, and 30% of the total thickness.

In accordance with certain embodiments of the invention, the hydroentangled composite includes a first outer surface, a second outer surface, and an interior region including a mid-point between the first outer surface and the second outer surface in the z-direction. In accordance with certain embodiments of the invention, a first concentration of the plurality of cellulose fibers at the first outer surface and/or the second outer surface is less than a second concentration of the plurality of the cellulose fibers at the mid-point.

In accordance with certain embodiments of the invention, the hydroentangled composite has a ratio between the basis weight (gsm) and the at least one core layer thickness (mm) in the z-direction from about 150:1 to about 350:1, such as from at least about any of the following: 150:1, 175:1, 200:1, 225:1, and 250:1 and/or from at most about any of the following: 350:1, 325:1, 300:1, 275:1, and 250:1.

In accordance with certain embodiments of the invention, the hydroentangled composite has a Rewet value of less than about 1 g, such as less than about 0.9 g, 0.8 g, 0.7 g. 0.6 g, 0.5 g, 0.4 g, or 0.3 g as determined by Hytec Annex TM04P modified only by using increased gush volumes for each of the two (2) to four (4) gushes of liquid (i.e., urine solution according to Annex TM04 P). For example, each of the two (2) to four (4) gushes of liquid may independently be selected from 30, 40, 50, 55, 60, 65, 70, 75, 80, 85, 90, 95, and 100 ml. The individual gush volumes, for instance, may vary by diaper size and test subsets of Rewet-TM04_02, and Combined acquisition time/Rewet TM04_09.

The hydroentangled composite, in accordance with certain embodiments of the invention, has a run-off value of less than about 60% as determined by ISO 9073-11, such as at most about any of the following: 60%, 55%, 50%, 40%, 35%, 30%, 25%, and 20% as determined by ISO 9073-11 and/or at least about any of the following: 5%, 10%, 12%, 15%, 20%, and 25% as determined by ISO 9073-11.

The hydroentangled composite, in accordance with certain embodiments of the invention, has an absorption capacity of at least 1500% as determined by ISO 9073, such as at most about any of the following: 1500%, 1400%, 1300%, 1200%, 1100%, 1000%, 950%, 900%, 875%, 850%, 825%, and 800% as determined by ISO 9073 and/or at least about any of the following: 500%, 550%, 600%, 700%, and 725% as determined by ISO 9073.

The hydroentangled composite, in accordance with certain embodiments of the invention, has a rate of absorption of less than about 12 seconds for a 5 ml liquid sample as determined by D824-94, such as at most about any of the following: 12, 10, 9, 8, 7, and 6 seconds as determined by D824-94 and/or at least about any of the following: 4, 5, 6, 7, and 8 second as determined by D824-94.

In accordance with certain embodiments of the invention, the plurality of raised portions comprise from about 25% to about 75% of a plan view of the first outermost surface, such as at least about any of the following: 25, 30, 35, 40, 45, 50, and 55% and/or at most about any of the following: 75, 70, 65, 60, 55, 50, and 45%. Additionally or alternatively, the plurality of recessed portions comprise from about 25% to about 75% of a plan view of the first outermost surface, such as at least about any of the following: 25, 30, 35, 40, 45, 50, and 55% and/or at most about any of the following: 75, 70, 65, 60, 55, 50, and 45%. In accordance with certain embodiments of the invention an average closest distance between adjacent raised portions may comprise from about 0.2 mm to about 5 mm, such as at least about any of the following: 0.2, 0.2, 0.4, 0.5, 0.8, 1, 1.2, 1.5, 1.6, 1.8, 2, 2.2, and 2.5 mm and/or at most about any of the following: 5, 4.8, 4.5, 4.2, 4, 3.8, 3.5, 3.2, 3, 2.8, 2.5, 2.2, and 2 mm. In accordance with certain embodiments of the invention, the average closest distance between adjacent raised portions may be defined by a shortest distance between a first peak of a first raised portion and a second peak of a second raised portion, in which the first raised portion and the second raised portion are adjacent each other with the exception of a single recessed portion therebetween, and comprise from about 0.2 mm to about 5 mm, such as at least about any of the following: 0.2, 0.2, 0.4, 0.5, 0.8, 1, 1.2, 1.5, 1.6, 1.8, 2, 2.2, and 2.5 mm and/or at most about any of the following: 5, 4.8, 4.5, 4.2, 4, 3.8, 3.5, 3.2, 3, 2.8, 2.5, 2.2, and 2 mm.

In accordance with certain embodiments of the invention, the plurality of raised portions comprise an average height from about 0.5 mm to about 5 mm, such as at least about any of the following: 0.5, 0.8, 1, 1.2, 1.5, 1.8, and 2 mm and/or at most about any of the following: 5, 4.8, 4.5, 4.2, 4, 3.8, 3.5, 3.2, 3, 2.8, 2.5, 2.2, and 2 mm; wherein the average height is defined as the average distance between respective peaks of the plurality of raised portions to respective plurality of recessed portions.

In accordance with certain embodiments of the invention, the three-dimensional topography may comprise, for example, a pattern of repeating rows of the plurality of raised portions and repeating rows of the plurality of recessed portions. In accordance with certain embodiments of the invention, the plurality of raised portions may extend across the hydroentangled composite at an angle from about 0% to about 90% from the machine direction or cross-direction, such as from at least about any of the following: 0, 5, 10, 15, 20, 25, 30, 35, 40, 45, and 50% from the machine direction and/or at least about any of the following: 90, 85, 80, 75, 70, 65, 60, 55, and 50% from the machine direction. In this regard, for instance, the hydroentangled composite may efficiently distribute a fluid striking the hydroentangled composite in both the x-direction and y-direction of the hydroentangled composite.

In accordance with certain embodiments of the invention, the hydroentangled composite may comprise a plurality of apertures that extend through the total thickness of the hydroentangled composite. For example, the plurality of apertures may be located in the plurality of recessed portions. In accordance with certain embodiments of the invention, for example, the plurality of apertures may comprise from about 1% to about 30% of a recessed area defined by the plurality of recessed portions, such as at least about any of the following: 1, 3, 5, 8, 10, 12, 15, 18, and 20% and/or at most about any of the following: 30, 28, 25, 22, 20, 18, and 15%. The plurality of apertures, in accordance with certain embodiments of the invention, may have an average diameter from about 0.2 mm to about 1.5 mm, such as at least about any of the following: 0.2, 0.3, 0.4, 0.5, 0.6, 0.7, 0.8, 0.9, and 1 mm and/or at most about any of the following: 1.5, 1.4, 1.3, 1.2, 1.1, and 1 mm. The plurality of apertures, in accordance with certain embodiments of the invention, may comprise an average area from about 0.4 $mm^2$ to about 0.8 $mm^2$, such as at least about any of the following: 0.4, 0.45, 0.5, and 0.55 $mm^2$ and/or at most about any of the following: 0.8, 0.75, 0.7, 0.65, 0.6, and 0.55 mm$^2$. In accordance with certain embodiments of the invention, the plurality of apertures may comprise a circular cross-section. For example, the plurality of apertures may have an average aspect ratio of from 0.8 to 1.2, such as at least about any of the following: 0.8, 0.85, 0.9, 0.95, and 1.0 and/or at most about any of the following: 1.2, 1.15, 1.1, 1.05, and 1.0.

In accordance with certain embodiments of the invention, the plurality of recessed portions has an average width between adjacent raised portions, and the average diameter of the plurality of apertures comprises a value that is from about 10% to about 75% of the average width between adjacent raised portions, such as at least about 10, 15, 20, 25, 30, 35, 40, 45, and 50% of the average width between adjacent raised portions and/or at most about any of the following: 75, 70, 65, 60, 55, 50, 45, and 40% of the average width between adjacent raised portions.

In accordance with certain embodiment of the invention, the hydroentangled composite may have varying average number of apertures per unit area of the hydroentangled composite (e.g., number of apertures per mm$^2$). For example, the hydroentangled composite may include from about 0.1 to about 0.8 apertures per mm$^2$, such as at least about any of the following: 0.1, 0.12, 0.14, 0.16, 0.18, 0.2, 0.2, 0.25, 0.28, 0.3, 0.32, 0.35, 0.38, 0.4, 0.42, 0.45, 0.48, 0.5, 0.52, 0.55, 0.58, or 0.6 number of apertures per mm$^2$, and/or at most about any of the following: 0.8, 0.78, 0.75, 0.72, 0.7, 0.68, 0.65, 0.62, and 0.6 number of apertures per mm$^2$.

In accordance with certain embodiments of the invention, the plurality of apertures may define an open area in the x-y plane (e.g., a plane defined by the machine direction and cross-direction of the hydroentangled composite) that comprise from about 3% to a about 25%, such as at least about any of the following: 3, 5, 6, 8, 10, 12, 15, and 18% and/or at most about any of the following: 25, 22, 20, 18, and 15%.

In accordance with certain embodiments of the invention, the hydroentangled composite has a ratio between rewet (g) to basis weight (gsm) from about $1.25 \times 10^{-3}$ to about $3.75 \times 10^{-3}$, such as from at least about any of the following: $1.25 \times 10^{-3}$, $1.5 \times 10^{-3}$, $1.75 \times 10^{-3}$, $2 \times 10^{-3}$, $2.25 \times 10^{-3}$, $2.5 \times 10^{-3}$, and $2.75 \times 10^{-3}$ and/or from at most about any of the following: $3.75 \times 10^{-3}$, $3.5 \times 10^{-3}$, $3.25 \times 10^{-3}$, $3 \times 10^{-3}$, and $2.75 \times 10^{-3}$.

In accordance with certain embodiments of the invention, the hydroentangled composite has a ratio between liquid strike through time (s) to basis weight (gsm) from about 2 to about 4, such as from at least about any of the following: 2, 2.25, 2.5, 2.75, and 3 and/or from at most about any of the following: 4, 3.75, 3.5, 3.25, and 3.

In accordance with certain aspects of the invention, the one or more the individual layers forming the hydroentangled composite or the hydroentangled composite in its entirety may be treated with a surfactant. For example, the first outer layer may be treated with a surfactant prior to being incorporated into the hydroentangled composite. In accordance with certain embodiments of the invention, the hydroentangled composite may be treated with a surfactant. The hydroentangled composite, for instance, may have a surfactant applied to at least a first outer surface of the hydroentangled composite. For instance, the surfactant may be applied by spraying or kiss-roll application. In accordance with certain embodiments of the invention, the hydroentangled composite may comprise from about 0.5 to about 3 wt. % of surfactant based on the entire weight of the hydroentangled composite. In accordance with certain embodiments of the invention, the surfactant may comprise a cationic surfactant, an anionic surfactant, a non-ionic surfactant, or any combinations thereof. In accordance with certain embodiments of the invention, the surfactant imparts hydrophilicity to one or more of the fibers of the hydroentangled composite. In this regard, the surfactant may improve liquid strike-through performance for the hydroentangled composite, which may be particularly desirable when used as an ADL in an absorbent article. A few non-limiting examples of suitable surfactants include, for example, Schill & Seilacher Aa (e.g., Silastol PHP 26, Silastol PHP 90, & Silastol 163) and Pulcra Chemicals (e.g., Stanex S 6327, Stantex S 6087-4, & A blend of rights-protected synthetic surfactant solutions commercially available from Stantex PP 602). An example of a synthetic surfactant that has been widely used in commercial topsheet finishes would be Triton GR-5M, an anionic sulfosuccinate surfactant produced by Dow Chemical Company. Another type of surfactant that may be useful is based on fatty acid polyethylene glycol esters. In accordance with certain embodiments of the invention, the surfactant comprises a fatty acid ester. In accordance with certain embodiments of the invention, one or more of the layers forming the hydroentangled composite may be devoid of a surfactant. For example, each and every layer forming the hydroentangled composite may be devoid of a surfactant. The hydroentangled composite, in accordance with certain embodiments of the invention, may be devoid of a surfactant.

In another aspect the present invention provides a method of making an ADL including steps of (a) providing a first outer layer (e.g., nonwoven web or nonwoven fabric) including a first plurality of synthetic fibers; (b) providing a second outer layer including a second plurality of synthetic fibers; (c) providing at least one core layer including cellulose fibers comprising natural cellulose fibers, synthetic cellulose fibers, or a combination thereof, wherein the at least one core layer is located directly or indirectly between the first outer layer and the second outer layer; (d) physically entangling the first plurality of synthetic fibers, the second plurality of synthetic fibers, and the cellulose fibers are physically entangled together to form a hydroentangled composite; and (e) imparting a three-dimensional topography defined by a first outermost surface of the hydroentangled composite; wherein the three-dimensional topography includes a plurality raised portions and a plurality of recessed portions.

In accordance with certain embodiments of the invention, the method may further comprise depositing the at least one core layer on top of the first outer layer (e.g., nonwoven web or nonwoven fabric) and depositing the second outer layer (e.g., nonwoven web or nonwoven fabric) on top of the at least one core layer prior to the step of physically entangling. In this regard, the method may comprise forming at least a three-layer nonwoven web prior to being physically entangled (e.g., hydroentangled, air-entangled, or combination thereof), in which the first plurality of synthetic fibers, the second plurality of synthetic fibers, and the cellulose fibers are physically entangled together to form a hydroentangled composite. In accordance with certain embodiments of the invention, the steps of physically entangling and imparting a three-dimensional topography may occur at least partially simultaneously.

In accordance with certain embodiments of the invention, the method may further comprise (a) providing a three-dimensional image transfer device having an imaging surface, (b) supporting the first outer layer on the imaging surface of the three-dimensional image transfer device, and (c) imparting the three-dimensional topography by subjecting at least the second outer layer to jets of fluid at a pressure sufficient to physically entangle the first plurality of synthetic fibers, the second plurality of synthetic fibers, and the cellulose fibers and to impart a three-dimensional image into the hydroentangled composite.

In accordance with certain embodiments of the invention, suitable three-dimensional imaging devices may comprise imaging sleeves include those described, for example, in RE38,105 and RE38,505, in which the contents of both are hereby incorporated by reference in their entirety. For example, the nonwoven fabric may include a three-dimensional image formed therein that may be formed throughout the nonwoven fabric. For example, the image transfer device may comprise one or more drums or even one or more sleeves affixed to a corresponding drum. One or more water jets, for example, may be applied to a side of the nonwoven opposite to the side contacting the image transfer device. Without intending to be bound by the theory, the one or more water jets and water directed through the nonwoven causes the fibers of the nonwoven to become displaced according to the image on the image transfer device such as the image formed on one or more drums or one or more sleeves affixed to a corresponding drum causing a three-dimensional pattern to be imaged throughout the nonwoven according to such image. Such imaging techniques are further described in, for example, U.S. Pat. No. 6,314,627 entitled "Hydroentangled Fabric having Structured Surfaces"; U.S. Pat. No. 6,735,833 entitled "Nonwoven Fabrics having a Durable Three-Dimensional Image"; U.S. Pat. No. 6,903,034 entitled "Hydroentanglement of Continuous Polymer Filaments"; U.S. Pat. No. 7,091,140 entitled "Hydroentanglement of Continuous Polymer Filaments"; and U.S. Pat. No. 7,406,755 entitled "Hydroentanglement of Continuous Polymer Filaments" each of which are hereby incorporated by reference in their entirety herein by reference.

In accordance with certain embodiments of the invention, the step of imparting the three-dimensional topography by subjecting at least the second outer layer to jets of fluid at a pressure sufficient to physically entangle the first plurality of synthetic fibers, the second plurality of synthetic fibers, and the cellulose fibers and to impart a three-dimensional image into the hydroentangled composite comprises utilizing jets of fluid (e.g., water) at a pressure from about 1500 psi to about 3500 psi, such as at least about any of the following: 1500, 1600, 1800, 2000, 2200, and 2500 psi, and/or at most about any of the following: 3500, 3200, 3000, 2800, 2600, and 2500 psi.

In another aspect the present invention provides a hygiene article, such as a diaper. In accordance with certain embodiments of the invention, the hygiene article comprises a longitudinal axis and a transversal axis perpendicular to the longitudinal axis. The hygiene article further comprises an ADL, such as those described and disclosed herein, a liquid impermeable backsheet, and an absorbent core, in which the absorbent core is located at least partially between the ADL and the backsheet.

In accordance with certain embodiments of the invention, the hygiene article may further comprise comprising a liquid permeable topsheet, wherein the topsheet overlies the ADL. For example, the plurality of raised portions of the hydroentangled composite extend outwardly towards the topsheet. The hygiene article, in accordance with certain embodiments of the invention, may further include a liquid impermeable backsheet comprising a film. For example, the film may comprise a monolithic film or a microporous film.

In accordance with certain embodiments of the invention, the absorbent core comprises an absorbent material. For example, the absorbent material may comprise from about 80% to about 100% of superabsorbent polymers by total weight of the absorbent material.

EXAMPLES

The present disclosure is further illustrated by the following examples, which in no way should be construed as being limiting. That is, the specific features described in the following examples are merely illustrative and not limiting.

Example Set (1)

Comparative Example 1-1

Figure 2A:
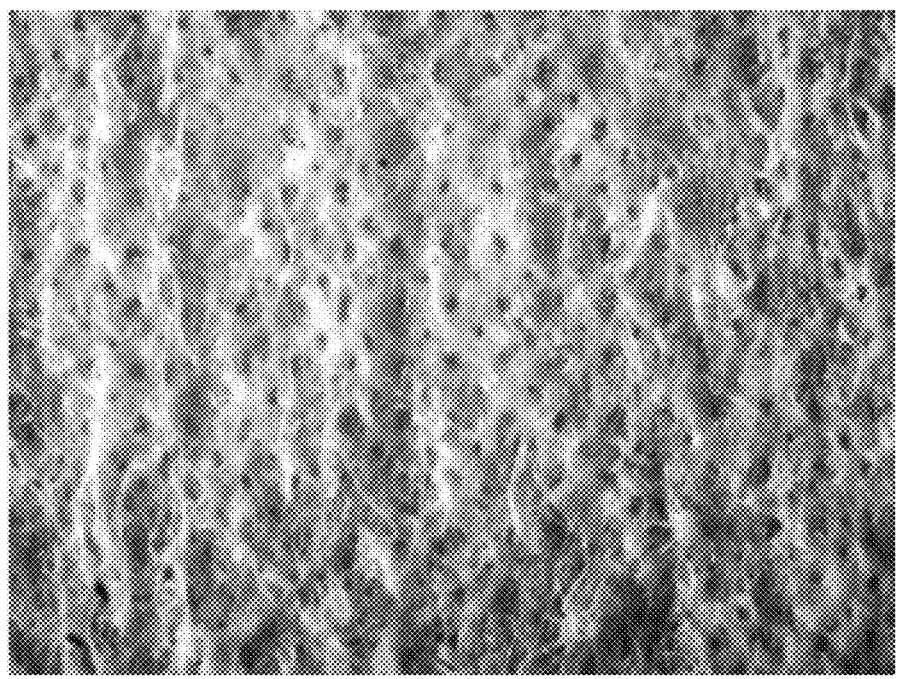
FIG. 2A illustrates a plan view of a 60 gsm hydroentangled composite that does not include a three-dimensional topography.
Figure 2B:
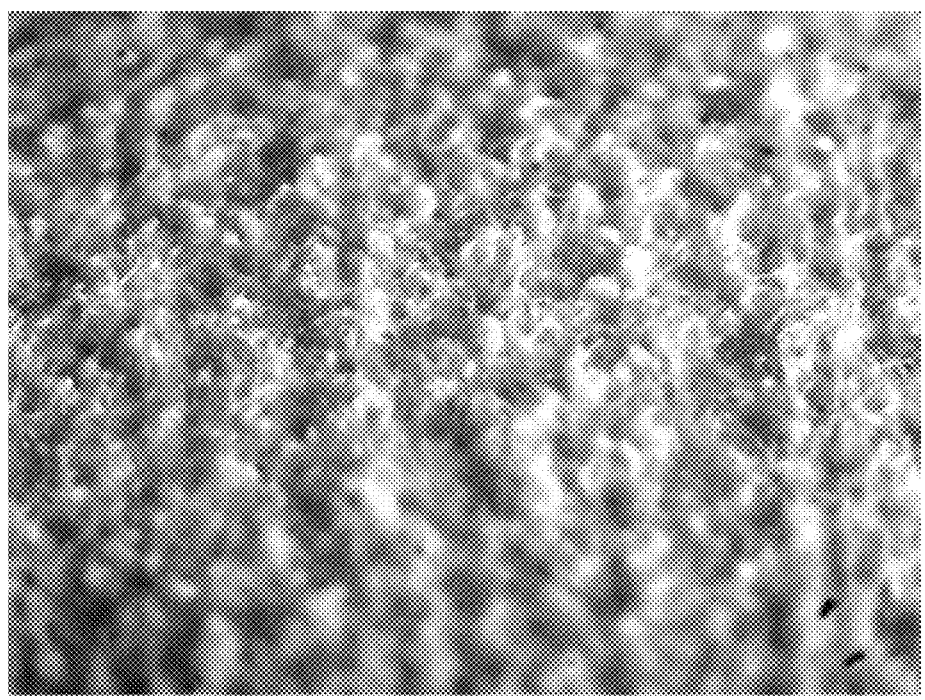
FIG. 2B illustrates an oblique view of the hydroentangled composite of FIG. 2A.

A 60 gsm hydroentangled composite was formed from two outer spunbond layers and a core layer of pulp. Each spunbond layer was formed from polypropylene and had a basis weight or about 10 gsm. The core layer of pulp had a basis weight of about 40 gsm. The three layers were subjected to a hydroentangling process to form the hydroentangled composite. The hydroentangled composite was not subjected to imaging and apertures were not imparted into the hydroentangled composite. FIG. 2A illustrates a plan view of the 60 gsm hydroentangled composite that does not include a three-dimensional topography or apertures therein. FIG. 2B illustrates an oblique view of the hydroentangled composite of FIG. 2A.

Example 1-1

Figure 3A:
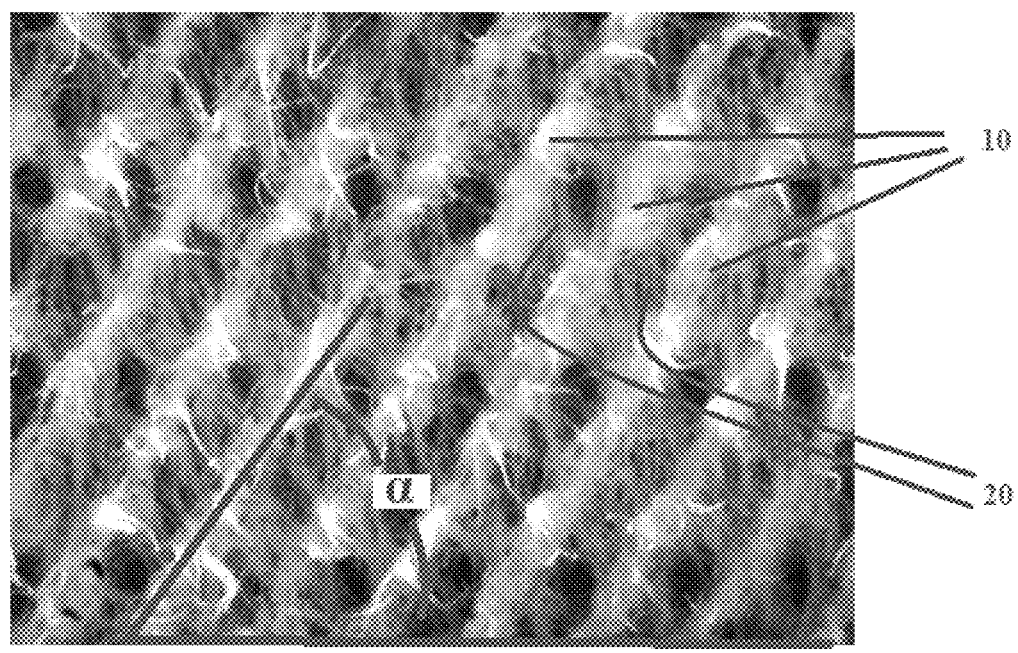
FIG. 3A illustrates a plan view of a 60 gsm hydroentangled composite, in accordance with certain embodiments of the invention, that includes a three-dimensional topography imparted thereto.
Figure 3B:
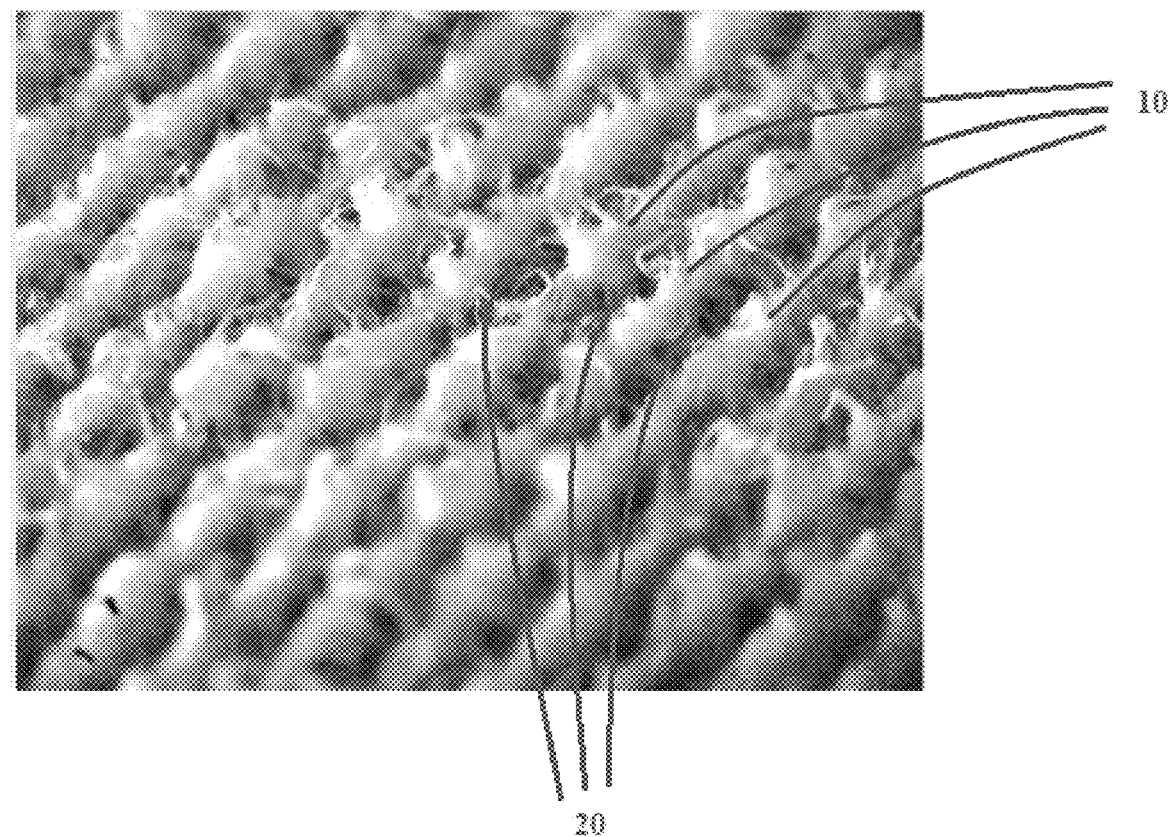
FIG. 3B illustrates an oblique view of the hydroentangled composite of FIG. 3A.

A 60 gsm hydroentangled composite was formed from two outer spunbond layers and a core layer of pulp. Each spunbond layer was formed from polypropylene and had a basis weight or about 10 gsm. The core layer of pulp had a basis weight of about 40 gsm. The three layers were subjected to a hydroentangling process to form a hydroentangled composite in the same manner as Comparative Example 1. For this example, however, the hydroentangled composite was further subjected to imaging via a three-dimensional image transfer device having an imaging surface, in which a three-dimensional topography was imparted into the hydroentangled composite by subjecting at least one outer layer of the hydroentangled composite to jets of fluid at a pressure sufficient impart the three-dimensional image into the hydroentangled composite. FIG. 3A illustrates a plan view of the 60 gsm hydroentangled composite that includes the three-dimensional topography imparted thereto. FIG. 3B illustrates an oblique view of the hydroentangled composite of FIG. 3A. The three-dimensional image of this example may be referred to as a Left Hand Twill image including a plurality raised portions 10 and a plurality of recessed portions 20. The average closest distance between adjacent raised portions was about 1.6 mm. FIG. 3A also illustrates that the plurality of raised portions extend across the hydroentangled composite at angle 'a' from a cross-direction or machine direction of the hydroentangled composite. As noted above, the plurality of raised portions may extend across the hydroentangled composite at an angle from about 0% to about 90% from the machine direction or the cross-direction, such as from at least about any of the following: 0, 5, 10, 15, 20, 25, 30, 35, 40, 45, and 50% from the machine direction or cross-direction and/or at least about any of the following: 90, 85, 80, 75, 70, 65, 60, 55, and 50% from the machine direction or the cross-direction.

Example 1-2

Figure 4A:
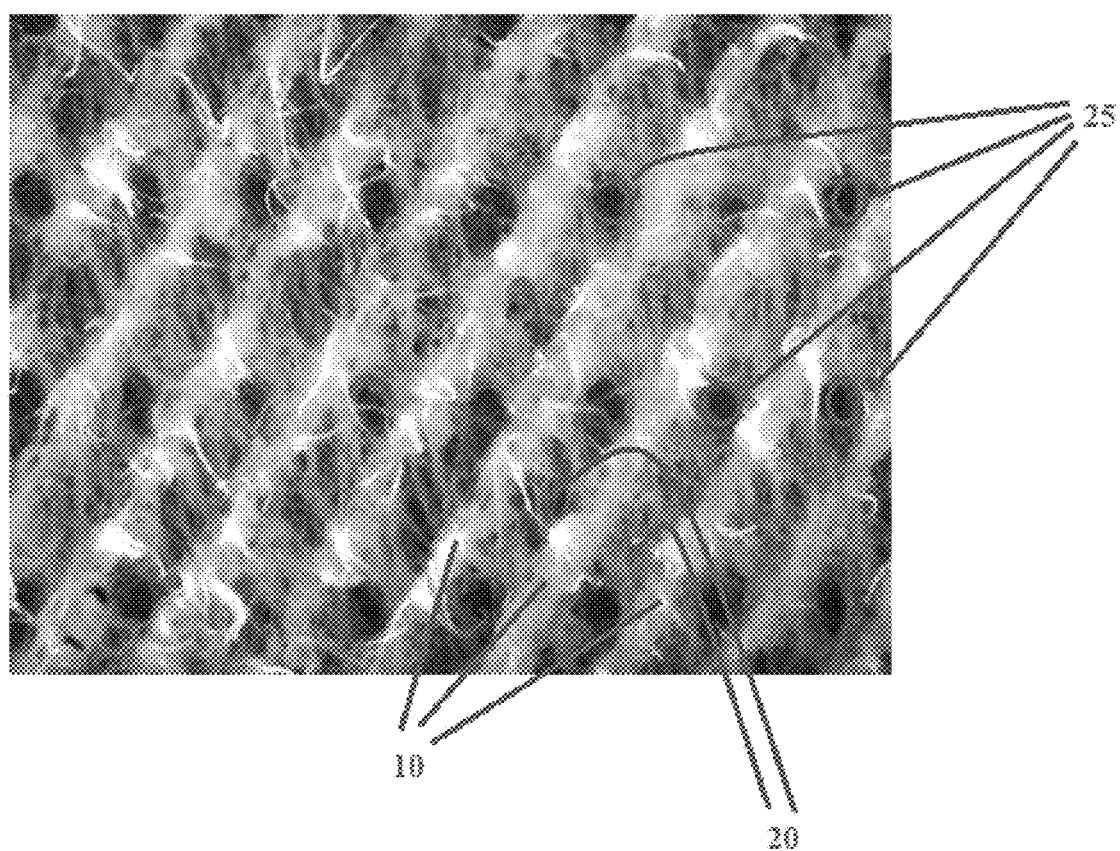
FIG. 4A illustrates a plan view of a 60 gsm hydroentangled composite, in accordance with certain embodiments of the invention, that includes a three-dimensional topography imparted thereto as well as a plurality of apertures located within valley portions of the hydroentangled composite.
Figure 4B:
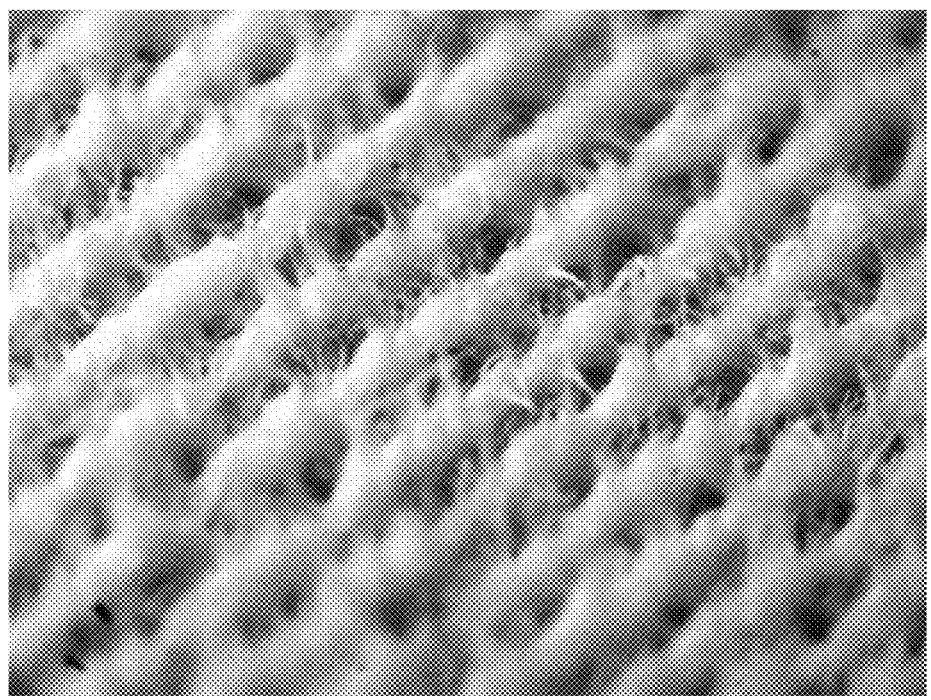
FIG. 4B illustrates an oblique view of the hydroentangled composite of FIG. 4A.

A 60 gsm hydroentangled composite was formed in an identical manner as Example 1-1. However, the imaging operation included the further formation of a plurality of apertures extending through the thickness of the hydroentangled composite. FIG. 4A illustrates a plan view of the 60 gsm hydroentangled composite that includes the three-dimensional topography imparted thereto as well as a plurality of apertures located within the plurality of recessed portions. FIG. 4B illustrates an oblique view of the hydroentangled composite of FIG. 4A. The three-dimensional image of this example includes a plurality raised portions 10, a plurality of recessed portions 20, and a plurality of apertures 25. The average diameter for the apertures was about 0.8 mm, while the average closest distance between adjacent raised portions was about 1.6 mm.

Example Set (2)

Comparative Example 2-1

A commercially available diaper having a construction illustrated by FIG. 5 was utilized as a baseline for comparing diapers having a construction in accordance with certain embodiments of the invention. As shown in FIG. 5, the diaper construction of this comparative example includes a top sheet (TS), a layer of glue, an acquisition layer (AQL) formed from a polyethylene terephthalate along with curly pulp (CS10), another glue layer, a core wrap (CWT) around a core (e.g., including a superabsorbent polymer), another glue layer, an additional film layer, another glue layer, a backsheet (BS), and a barrier layer cuff (BLC) to control leakage along the edge. The AQL/CS10 layers combined for a basis weight of 52 gsm.

This comparative example (i.e., the commercially available diaper) was tested for Rewet and Liquid Strike Through Time (LSTT) as described herein after being deconstructed and reconstructed to ensure the same testing procedures with the examples discussed below. That is, the testing of this comparative example and the examples below may be referred to as "disturbed" testing.

Example 2-1

The commercially available diaper from Comparative Example 2-1 was deconstructed and the AQL/SC10 layers were removed and replaced with an ADL layer in accordance with certain embodiments of the invention. In this regard, the combination of the two AQL/SC10 layers was replaced with a single hydroentangled composite. The hydroentangled composite comprised a spunbond-pulp-spunbond material that was mechanically entangled together to provide the hydroentangled composite. The hydroentangled composite was used to replace the two AQL/SC10 layers and the diaper was reconstructed to enable testing. FIG. 6 illustrates the diaper construction of this example.

The hydroentangled composite had a total basis weight of 80 gsm, in which the pulp content accounts for about 60 gsm and each spunbond layer accounted for about 10 gsm. The hydroentangled composite has a similar three-dimensional topography as that of Examples 1-1 and 1-2. The hydroentangled composite of this example included an open area of about 9% defined by the plurality of apertures formed therein. The average area of the plurality of apertures was 0.56 mm$^2$ and a the number of apertures per mm$^2$ of the hydroentangled composite was 0.16. FIG. 7 shows the hydroentangled composite including a plurality raised portions 10, a plurality of recessed portions 20, and a plurality of apertures 25.

The diaper of Example 2-1 was tested for Rewet and Liquid Strike Through Time (LSTT) as described herein.

Example 2-2

This example was prepared in an identical manner as that of Example 2-1, but the hydroentangled composite was treated with a fatty acid ester surfactant commercially available as Stantex S 6327 from Pulcra Chemicals. The surfactant accounted for 1% by weight of the hydroentangled composite.

The diaper of Example 2-2 was tested for Rewet and Liquid Strike Through Time (LSTT) as described herein.

Example 2-3

This example was prepared in an identical manner as that of Example 2-1, but the hydroentangled composite has an open area of 18% and the plurality of apertures had an average area of 0.5 mm$^2$. The number of apertures per mm$^2$ of the hydroentangled composite was 0.32. FIG. 8 shows the hydroentangled composite including a plurality raised portions 10, a plurality of recessed portions 20, and a plurality of apertures 25.

The diaper of Example 2-3 was tested for Rewet and Liquid Strike Through Time (LSTT) as described herein.

Example 2-4

This example was prepared in an identical manner as that of Example 2-3, but the hydroentangled composite was treated with a fatty acid ester surfactant commercially available as Stantex S 6327 from Pulcra Chemicals. The surfactant accounted for 1% by weight of the hydroentangled composite.

The diaper of Example 2-4 was tested for Rewet and Liquid Strike Through Time (LSTT) as described herein.

Table 1 provides a summary of the respective rewet and liquid strike through times for the diapers of Example Set (2). Table 1, for instance, illustrates that diapers including a hydroentangled composite in accordance with certain embodiments of the invention have vastly improved rewet values. In this regard, the LSTT values of hydroentangled composites in accordance with certain embodiments of the invention may have slightly increased values. However, the addition of a minor amount of surfactant has been shown to reduce the LSTT values while not significantly losing the increased performance in rewet performance. In this regard, for example, the combination of % open area defined by suitably sized apertures within the context of a hydroentangled composite having a three-dimensional topography and a minor addition of surfactant (e.g., 1%, 1.5%, or 2% by weight of the hydroentangled composite) may provide improved rewet performance and similar or the same LSTT performance in accordance with certain embodiments of the invention.

Example 2-5

This example was prepared in an identical manner as that of Example 2-1, but the hydroentangled composite included more holes per mm², namely 0.55 holes per mm². Additionally, the hydroentangled composite was not treated with any surfactant. That is, the hydroentangled composite was devoid of a surfactant.

The diaper of Example 2-5 was tested for Rewet and Liquid Strike Through Time (LSTT) as described herein.

Example 2-6

This example was prepared in an identical manner as that of Example 2-5, but the hydroentangled composite included more holes per mm², namely 0.64 holes per mm². Additionally, the hydroentangled composite was not treated with any surfactant. That is, the hydroentangled composite was devoid of a surfactant.

The diaper of Example 2-6 was tested for Rewet and Liquid Strike Through Time (LSTT) as described herein.

TABLE 1

| | Basis Weight (gsm) | Rewet (g) | Rewet % Change from Comparative Example 2-1 | Liquid Strike Through Time (LSTT) (s) | LSTT % Change from Comparative Example 2-1 |
|---|---|---|---|---|---|
| Comp. Example 2-1 | 52 | 0.4291 | NA | 188.2 | NA |
| Example 2-1 | 80 | 01.070 | −75% | 276.6 | 47% |
| Example 2-2 | 80 | 0.1297 | −70% | 251.0 | 33.4% |
| Example 2-3 | 80 | 0.1826 | −57.5% | 236.0 | 25.4% |
| Example 2-4 | 80 | 0.2553 | −40.5% | 204.0 | 8.4% |
| Example 2-5 | 60 | 0.3563 | −17.0% | 173.7 | −7.7% |
| Example 2-6 | 60 | 0.2394 | −44.2% | 176.73 | −6.1 |

These and other modifications and variations to embodiments of the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. An acquisition-distribution-layer (ADL), comprising:
a hydroentangled composite comprising (a) a first outer layer including a first plurality of synthetic fibers, (b) a second outer layer including a second plurality of synthetic fibers, and (c) at least one core layer including cellulose fibers comprising natural cellulose fibers, synthetic cellulose fibers, or a combination thereof, wherein the at least one core layer is located directly or indirectly between the first outer layer and the second outer layer, and the first plurality of synthetic fibers, the second plurality of synthetic fibers, and the cellulose fibers are physically entangled together;
the hydroentangled composite further comprises a three-dimensional topography throughout the hydroentangled composite, the three-dimensional topography is defined by a first outermost surface and a second outermost surface of the hydroentangled composite; wherein the three-dimensional topography includes a plurality of raised portions and a plurality of recessed portions; and wherein the hydroentagled composite has from 0.1 to 0.8 apertures per mm², the apertures extend through a total thickness of the hydroentangled composite from the first outermost surface to the second outermost surface.

2. The ADL of claim 1, wherein the hydroentangled composite comprises a basis weight from about 20 to about 100 grams-per-square (gsm).

3. The ADL of claim 1, wherein the first outer layer comprises a first spunbond layer and the second outer layer comprises a second spunbond layer.

4. The ADL of claim 1, wherein the at least one core layer comprises from about 40% by wt. to about 80% by wt. of the hydroentangled composite.

5. The ADL of claim 1, wherein the total thickness is orthogonal to a machine-direction and a cross-direction of the hydroentangled composite, and the at least one core layer comprises from about 10% to about 60% of the total thickness.

6. The ADL of claim 5, wherein the hydroentangled composite has a ratio between a basis weight (gsm) of the hydroentangled composite and the at least one core layer thickness (mm) in the z-direction from about 150:1 to about 350:1.

7. The ADL of claim 1, wherein the hydroentangled composite has a rewet value of less than about 1 g.

8. The ADL of claim 1, wherein the hydroentangled composite has a run-off value of less than about 60% as determined by ISO 9073-11.

9. The ADL of claim 1, wherein the hydroentangled composite has an absorption capacity of at least 1500% as determined by ISO 9073.

10. The ADL of claim 1, wherein the hydroentangled composite has a rate of absorption of less than about 12 seconds for a 5 ml liquid sample as determined by D824-94.

11. The ADL of claim 1, wherein the plurality of raised portions comprise from about 25% to about 75% of a plan view of the first outermost surface.

12. The ADL of claim 1, wherein the plurality of raised portions comprise an average height from about 0.5 mm to about 5 mm.

13. The ADL of claim 1, wherein the apertures are located in the plurality of recessed portions, and wherein the apertures comprise from about 1% to about 30% of a recessed area defined by the plurality of recessed portions.

14. A hygiene article, comprising:
a longitudinal axis;
a transversal axis perpendicular to the longitudinal axis;
an acquisition distribution layer (ADL) comprising a hydroentangled composite comprising (a) a first outer layer including a first plurality of synthetic fibers, (b) a second outer layer including a second plurality of synthetic fibers, and (c) at least one core layer including cellulose fibers comprising natural cellulose fibers, synthetic cellulose fibers, or a combination thereof, wherein the at least one core layer is located directly or indirectly between the first outer layer and the second outer layer, and the first plurality of synthetic fibers, the second plurality of synthetic fibers, and the cellulose fibers are physically entangled together;

a liquid impermeable backsheet; and an absorbent core, wherein the absorbent core is located at least partially between the ADL and the backsheet;

the hydroentangled composite further comprises a three-dimensional topography throughout the hydroentangled composite, the three-dimensional topography is defined by a first outermost surface and a second outermost surface of the hydroentangled composite; wherein the three-dimensional topography includes a plurality of raised portions and a plurality of recessed portions with an average closest distance between respective peaks of the plurality of raised portions from 0.2 mm to 5 mm, and wherein the hydroentagled composite has from 0.1 to 0.8 apertures per mm$^2$, the apertures extend through a total thickness of the hydroentangled composite.

15. The hygiene article of claim 14, further comprising a liquid permeable topsheet, wherein the topsheet overlies that ADL.

16. The hygiene article of claim 15, wherein the a plurality raised portions of the ADL extend outwardly towards the topsheet.

17. A method of making an ADL, comprising:

providing a first outer layer including a first plurality of synthetic fibers;

providing a second outer layer including a second plurality of synthetic fibers;

providing at least one core layer including cellulose fibers comprising natural cellulose fibers, synthetic cellulose fibers, or a combination thereof, wherein the at least one core layer is located directly or indirectly between the first outer layer and the second outer layer;

physically entangling the first plurality of synthetic fibers, the second plurality of synthetic fibers, and the cellulose fibers are physically entangled together to form a hydroentangled composite;

imparting a three-dimensional topography throughout the hydroentangled composite, the three-dimensional topography is defined by a first outermost surface and an opposing second outermost surface of the hydroentangled composite; wherein the three-dimensional topography includes a plurality raised portions and a plurality of recessed portions with an average closest distance between respective peaks of the plurality of raised portions from 0.2 mm to 5 mm; and imparting a plurality of apertures extending through a total thickness of the hydroentangled composite from the first outermost surface to the second outermost surface, wherein the hydroentagled composite has from 0.1 to 0.8 apertures per mm$^2$.

18. The method of claim 17, wherein the step of physically entangling the first plurality of synthetic fibers, the second plurality of synthetic fibers, and the cellulose fibers are physically entangled together comprises hydroentanglement, air entanglement, or any combination thereof.

19. The method of claim 17, wherein the steps of physically entangling and imparting a three-dimensional topography occur at least partially simultaneously.

20. The ADL of claim 1, wherein the plurality raised portions are continuous along an X-Y plane of the ADL and the plurality of recessed portions are continuous along the X-Y plane of the ADL, and wherein the plurality raised portions and the plurality of recessed portions are disposed in an alternating configuration.

21. The ADL of claim 1, wherein the plurality of raised portions and the plurality of recessed portions have an average closest distance between respective peaks of the plurality of raised portions from 0.2 mm to 5 mm.

* * * * *

UNITED STATES PATENT AND TRADEMARK OFFICE
CERTIFICATE OF CORRECTION

PATENT NO. : 12,233,633 B2  
APPLICATION NO. : 17/377828  
DATED : February 25, 2025  
INVENTOR(S) : Ralph A. Moody, III et al.

Page 1 of 1

It is certified that error appears in the above-identified patent and that said Letters Patent is hereby corrected as shown below:

In the Claims

In Column 17, Claim 1, Line 66, "hydroentagled composite" should read as -- hydroentangled composite --

In Column 19, Claim 14, Line 19, "hydroentagled" should read as -- hydroentangled --

In Column 19, Claim 16, Line 26, "wherein the a plurality raised" should read as -- wherein the plurality of raised --

In Column 20, Claim 17, Line 10, "plurality raised" should read as -- plurality of raised --

In Column 20, Claim 17, Line 18, "hydroentagled composite" should read as -- hydroentangled composite --

In Column 20, Claim 20, Line 27, "plurality raised" should read as -- plurality of raised --

In Column 20, Claim 20, Line 30, "plurality raised" should read as -- plurality of raised --

Signed and Sealed this  
Third Day of June, 2025

Coke Morgan Stewart  
*Acting Director of the United States Patent and Trademark Office*